United States Patent [19]

Erlandsson

[11] 4,106,511
[45] Aug. 15, 1978

[54] ELECTRICAL STIMULATOR IN REMEDY OF INCONTINENCE

[75] Inventor: Bjorn Erik Erlandsson, Göteborg, Sweden

[73] Assignee: Svenska Utvecklingsaktiebolaget, Stockholm, Sweden

[21] Appl. No.: 786,855

[22] Filed: Apr. 12, 1977

[30] Foreign Application Priority Data

Apr. 21, 1976 [SE] Sweden .............................. 7604553

[51] Int. Cl.² .............................................. A61N 1/04
[52] U.S. Cl. ..................................... 128/407; 128/422
[58] Field of Search ................ 128/407, 408, 421, 422

[56] References Cited

U.S. PATENT DOCUMENTS

| | | | |
|---|---|---|---|
| 2,532,788 | 12/1950 | Sarnoff | 128/421 |
| 3,563,247 | 2/1971 | Bowers | 128/422 |
| 3,589,370 | 6/1971 | McDonald | 128/422 |
| 3,640,284 | 2/1972 | De Langis | 128/422 |
| 3,650,275 | 3/1972 | von der Mozel | 128/422 |

FOREIGN PATENT DOCUMENTS

| | | | |
|---|---|---|---|
| 1,145,749 | 3/1969 | United Kingdom | 128/407 |
| 230,967 | 5/1925 | United Kingdom | 128/407 |

*Primary Examiner*—William E. Kamm
*Attorney, Agent, or Firm*—Holman & Stern

[57] ABSTRACT

An electrical stimulator is provided for controlling the urethral — the bladder and/or the rectal function. Said stimulator comprises an obturator to be worn within the vagina or anus. The obturator is made of a flexible material, which can be expanded for providing a safe fixation of the obturator within the body. The obturator is provided with electrodes energized by a pulse generator, said electrodes are arranged in two groups, which are directed towards the same direction, e.g. towards urethra, and thus providing a directional stimulating effect. The pulse generator provides an intermittent stimulation with a biphasic pulse form and with a gradually increasing pulse amplitude up to an adjusted maximum amplitude during each unit of stimulation pulses.

17 Claims, 10 Drawing Figures

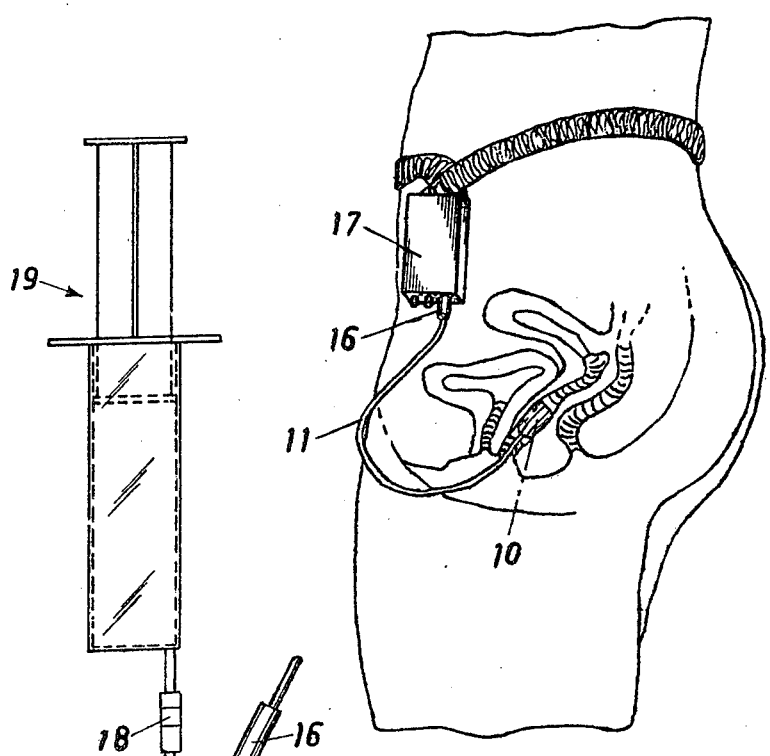
FIG.1
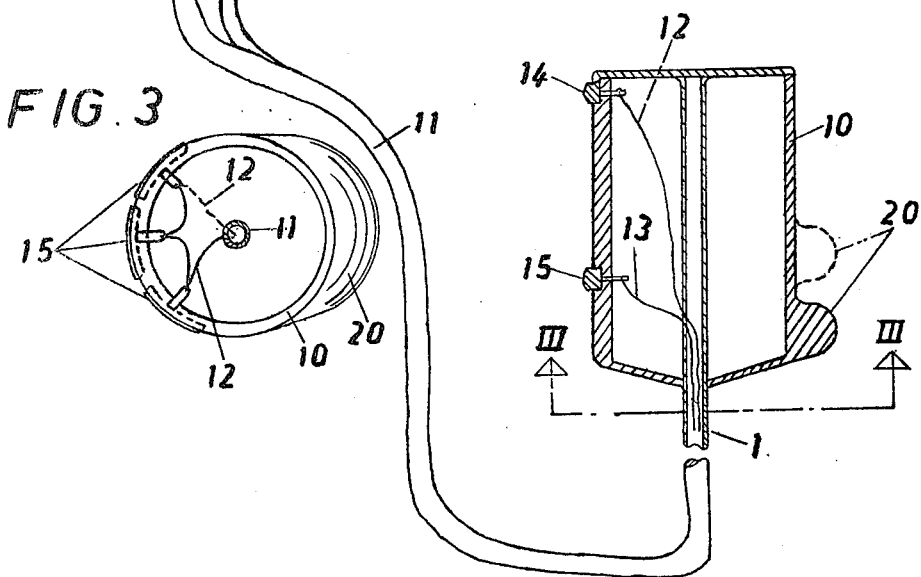
FIG.2
FIG.3

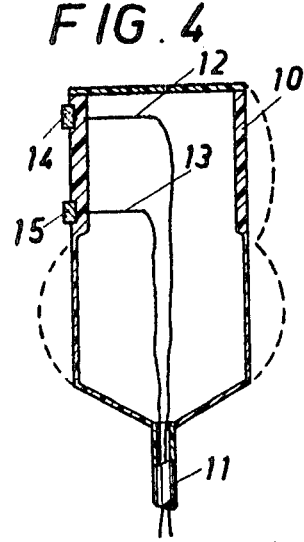
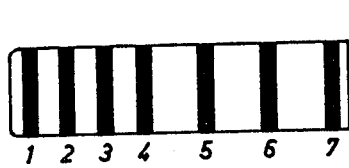
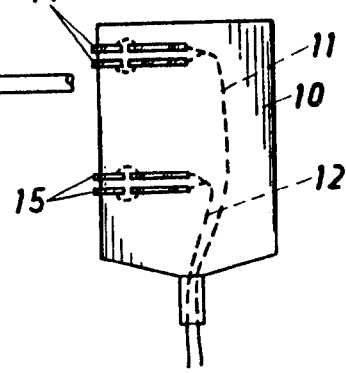
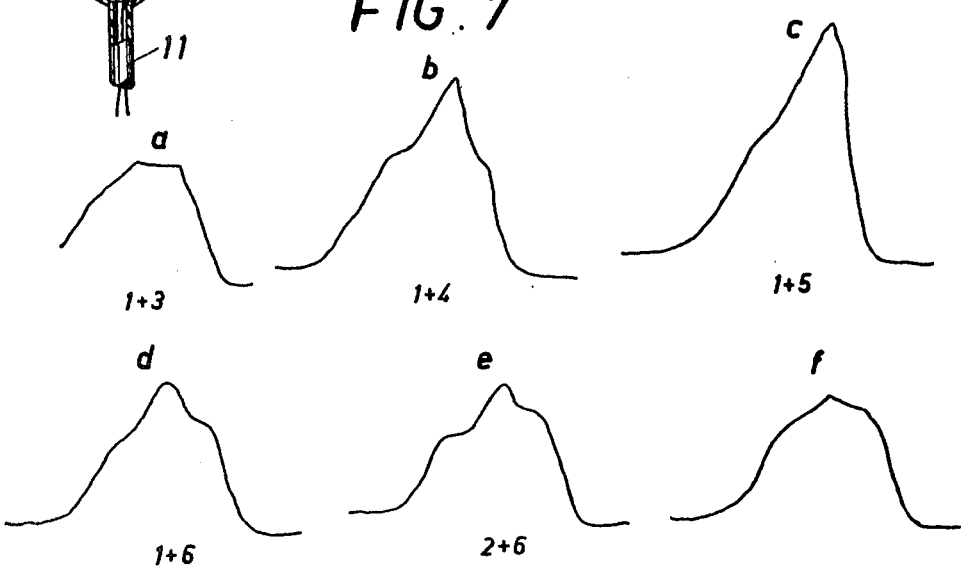
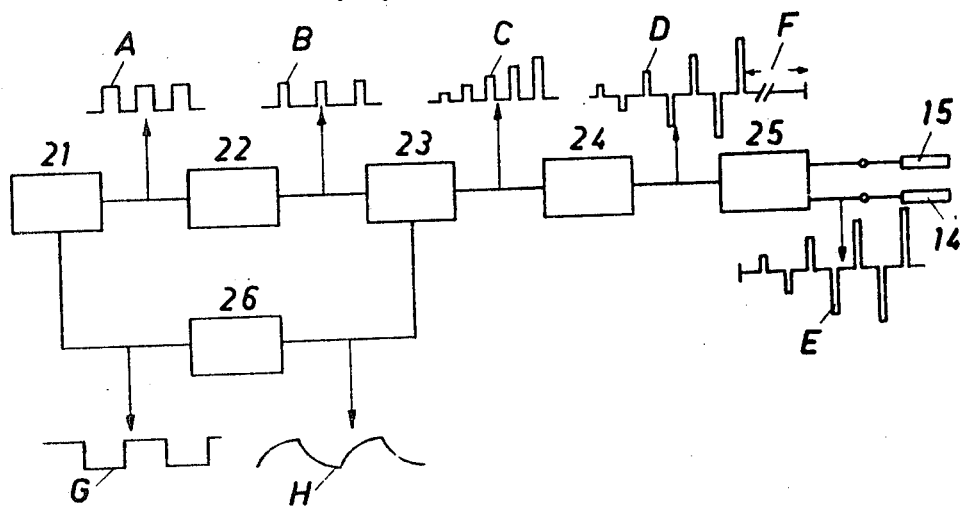

ELECTRICAL STIMULATOR IN REMEDY OF INCONTINENCE

BACKGROUND OF THE INVENTION

The present invention refers to an electrical stimulator comprising an obturator intended to be worn within the vagina or anus, said obturator being provided with electrodes energized by a pulse generator and thereby controlling the urethral-, the bladder and/or the rectal function, and said obturator being made of a flexible material, which is expandable and thus provides a safe fixation of the obturator within the body.

Disorders of the bladder function is a big problem for the individual as well as for the medical service. Urinary incontinence is very frequent and requires a lot of time for the nursing considering change of clothes, bedclothes etc.

Efforts have been made for solving these problems in many different ways, e.g. by means of technical means for collecting the urine, which works fairly satisfactory for men, but is more difficult to make with women. Efforts have also been made to electrically stimulate the pelvis floor by the implantation of electrodes into the pelvis floor muscles, said electrodes being connected to a receiver introduced into the body, said receiver electromagnetically being fed with impulses from a transmitter outside the body. This method requires a surgical operation and is relatively complicated and expensive.

According to another method urethra closure is achieved by electrical stimulation by means of electrodes placed on a intravaginal or intraanal plug of an appropriate shape. The plug is usually of rigid plastic and has a circular cross-section, and the electrodes consists of circumferential metal rings. The plug is rounded at the end being inserted into the body, whereby an exact placing and fixation of the plug in the body is difficult to achieve. Besides that it can be unpleasant to wear such a rigid plug in the body and there is a risk that the plug can slip out. Furthermore a relatively diffuse stimulation of the entire pelvic area is obtained by means of the circumferential electrodes.

SUMMARY OF THE INVENTION

The purpose of the present invention is to provide a stimulator of the above mentioned kind, which does not require a surgical operation for the application, which is easy to insert and remove and can be worn without inconvenience and which remains safely in place without the risk of slipping out. The electrodes shall with this stimulator be kept in a position, which on an examination has proved to be the most appropriate for the individual, and the stimulation shall be directed towards e.g. urethra or the bladder, at which it is of the utmost importance that an exact placing and fixation of the obturator is obtained in the body, e.g. contacting the os uteri.

This is according to the invention achieved by the obturator being provided with a substantially plane or somewhat curved end gable at its inner end as seen from its position of use, the electrodes being arranged in two groups arranged at a certain distance from each other, each group being electrically connected to the pulse generator and comprising a number of electrode plates connected in parallel and arranged in substantially the same plane, the electrode plates of both groups being directed towards the same direction and the electrode plates of each group extending over only a part of the circumference of the obturator for achieving a directional stimulating effect.

The obturator can be so designed that if in an unloaded state contains a very small amount of air, at which it can be easily inserted, after which it is inflated so that it remains safely in place. It can also be so designed that it in an unloaded position contains a larger amount of air, at which it has to be evacuated before it is inserted, after which it substantially recovers its original volume. Owing to that the obturator is made of a flexible material it is shaped after the space in which it is placed, and it can by reason of that be carried without inconvenience at the same time as it remains safely in place. When it is to be removed it is evacuated again and it can then be removed without any problems.

The device is at first hand intended as a remedy for female incontinence. An important group is women suffering from stress incontinence, i.e. leakage of urine when the abdomen pressure is rapidly increased as when coughing, sneezing and lifting. Another important group is women suffering from so called urge incontinence. Also other groups of incontinent patients can be treated with the device according to the invention. The device is also applicable to masculine incontinence, at which the obturator is introduced into the anus.

Since the device according to the invention is intended to be battery operated it is important that the energy consumption is low. Tests with intermittent stimulation have therefore been made. It has proved to be appropriate to have a stimulation period of about 8-12 seconds, after which a break of about 15-20 seconds follows etc. This procedure is then repeated as long as the pulse generator is switched on.

An intermittent stimulation gives the same effect upon urethra closure and bladder relaxation as a continuous stimulation, but results in the important advantage that the fatigue effect decreases. Other stimulation periods and breaks are of course possible within a relatively large range, e.g. stimulation and break periods each varying between 2 and 180 seconds. The most appropriate stimulation period is tried out for every individual.

In order to obstruct sensation of pain caused by the intermittent stimulation the electrical apparatus has been so designed, that during the about 1-2 first seconds of every stimulation period the pulse amplitude gradually increases to the adjusted maximum amplitude. The stimulation frequency is just about 5-60 Hz. For patients with stress incontinence a frequency of about 15-60 Hz is appropriate for achieving an effective urethra closure, while for patients with urgency incontinence a frequency of about 5-25 Hz is appropriate for achieving an effective bladder relaxation.

The tests which have been made have given a very good result. Some patients have after treatment during some time even become continent and independent of the stimulator.

BRIEF DESCRIPTION OF THE DRAWINGS

FIG. 1 shows the disposal of the stimulator within the body,

FIG. 2 is a vertical section through a stimulator according to an embodiment, and shows a flexible tube connected thereto, at the free end of which an evacuating- and inflating device is provided, FIG. 3 is a section according to the line III — III in FIG. 2, FIG. 4 is a section through a stimulator according to another embodiment, FIG. 5 shows a third embodiment of the stimulator, FIG. 6 shows schematically a testing device for trying out the most appropriate electrode positions for the individual, FIG. 7a-e shows the urethral pressure profiles from one patient with stimulation from different electrode pairs, FIG. 7f shows the urethral pressure profile without stimulation, FIG. 9 is a block diagram of the pulse generator.

DESCRIPTION OF THE PREFERRED EMBODIMENTS

Figure 8:
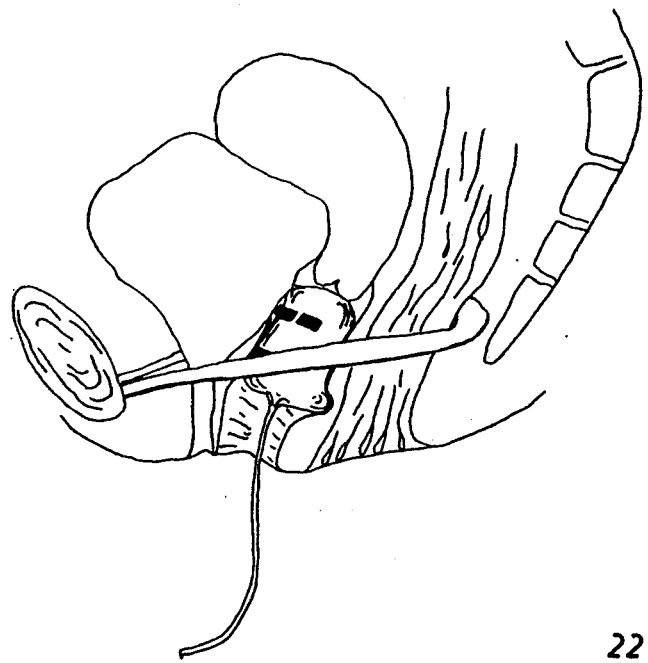
FIG. 8 is a schematic section through the pelvis area.

The device comprises an inflatable obturator 10 of a flexible material, which is kind to the tissues, e.g. silicon rubber. A flexible tube 11 is connected to the obturator 10. So that there shall be no risk for the tube 11 to come loose from the obturator 10, when the device is removed from the body, the tube 11 can be attached to the upper as well as to the lower end gable of the obturator 10, as shown in FIG. 2. Another possibility is to place threads of a tearproof material within the tube 11. These threads are attached to the upper end gable of the obturator 10.

A two-part cable is placed within the tube 11, the two wires 12 and 13 of said cable each being connected to a group of electrodes 14 and 15 resp., which are fixed to the obturator 10. As is shown in FIG. 3 each group of electrodes can be composed of a number of, e.g. three, small metal plates connected in parallel. The groups of electrodes 14 and 15 are located at the same side of the obturator 10 and extends across less than half the circumference of the obturator 10. With a correct insertion a stimulation directed towards e.g. urethra can be obtained.

Other radial extensions of the electrode groups are possible depending on whether a distinctly directional or a more diffusely directional stimulating effect is desirable. The extension of the electrode groups can correspond to a sector of about 80°-240°.

The wires 12 and 13 are at their free ends provided with a two-pole plug 16 for the connection to a battery operated pulse generator arranged in a small box 17, which can be carried close to the body, as is shown in FIG. 1.

At the free end of the tube 11 a hand operated nonreturn valve 18 is arranged, through which air can be blown into the obturator 10 and through which the obturator 10 can be evacuated. An inflating- and evacuating device 19 is shown in FIG. 2.

The obturator 10 according to the embodiment shown in FIGS. 2 and 3 has a thicker wall thickness on the side provided with the electrodes 14 and 15. By that the thinner wall section will be curved inwards when the obturator is evacuated, while the thicker wall section provided with the electrodes 14 and 15 keeps its bulged shape, at which the volume of the obturator 10 is considerably reduced and the insertion is made easier. Besides that the thicker wall section provides a good support for the electrodes 14 and 15.

As is previously mentioned the obturator 10 is inserted and removed in an evacuated state, while it is inflated when it is put in place.

According to the embodiment in FIGS. 2 and 3 the obturator 10 is provided with one or more bulges 20 on the side which is not provided with the electrodes. There is otherwise a small risk that the obturator 10 slips out when it is used by some patients. This risk can be eliminated by those bulges 20, which preferably consists of the same material as the rest of the obturator 10, e.g. silicon rubber.

The obturator 10 has a substantially plane end gable at its inner end as seen in the position of use. By that an exact placing and fixation of the obturator 10 within the body can be achieved, e.g. contacting the os uteri. This is of the utmost importance for obtaining a stimulation directed towards e.g. urethra. It would also be possible to have a somewhat curved, i.e. concave or convex, end gable.

According to the embodiment in FIG. 4 the obturator 10 at its lower part, which is not provided with the electrodes 14 and 15, has a thinner wall thickness compared with the upper part. By that a stronger bulging is obtained at the lower part of the obturator 10 at the expansion, as is indicated with broken lines. The obturator is by that prevented from slipping out. The side of the upper part of the obturator 10, which is not provided with the electrodes 14 and 15 has a thicker wall thickness than the lower part of the obturator 10 but a thinner wall thickness compared with the side provided with the electrodes 14 and 15.

According to the embodiment in FIG. 5 each group of electrodes 14 and 5 resp. consists of electrode plates connected in parallel and arranged in two rows. It would of course also be possible to arrange three or more rows of electrode plates connected in parallel for each group of electrodes 14 and 15.

The distance between the electrode groups 14 and 15 is of the utmost importance for the increase of the urethral pressure. This optimum distance varies from patient to patient and therefore a careful individual testing has to be made. In FIG. 6 a testing device for the determination of the optimum electrode placing is schematically shown, where the numerals 1-7 denotes groups of electrodes, which can be combined alternatively. In FIG. 7a-e urethral pressure profiles from a patient with some different electrode combinations are shown, and it can be seen that the electrode combination 1+5 in this case gave the best stimulating effect, while some other electrode combinations hardly gave any stimulating effect at all. Comparison shall herewith be made with FIG. 7e, in which the urethral pressure profile without electrostimulation is shown.

The above result is due to the fact that the nerves leading to the urethra muscles and the pelvis floor (see FIG. 8) can be stimulated in an efferent direction. Besides that these nerves lead impulses in an afferent direction to the spinal marrow, at which nerve reflexes actuating the urethra and the bladder are provoked. These reflexion mechanisms are very important for restoring the continence. The individual placing of the electrodes is very important for obtaining an optimum stimulation of the nerves. The electrode placing can e.g. be tested by means of the testing device shown in FIG. 6, so that an optimum stimulating effect is obtained.

The pulse generator comprises several electronic components, for which space saving and current saving integrated circuits of so called cmos-type preferably are used. As a current source e.g. mercury cells can be used, at which the voltage should be between 10-15V.

Figure 10:
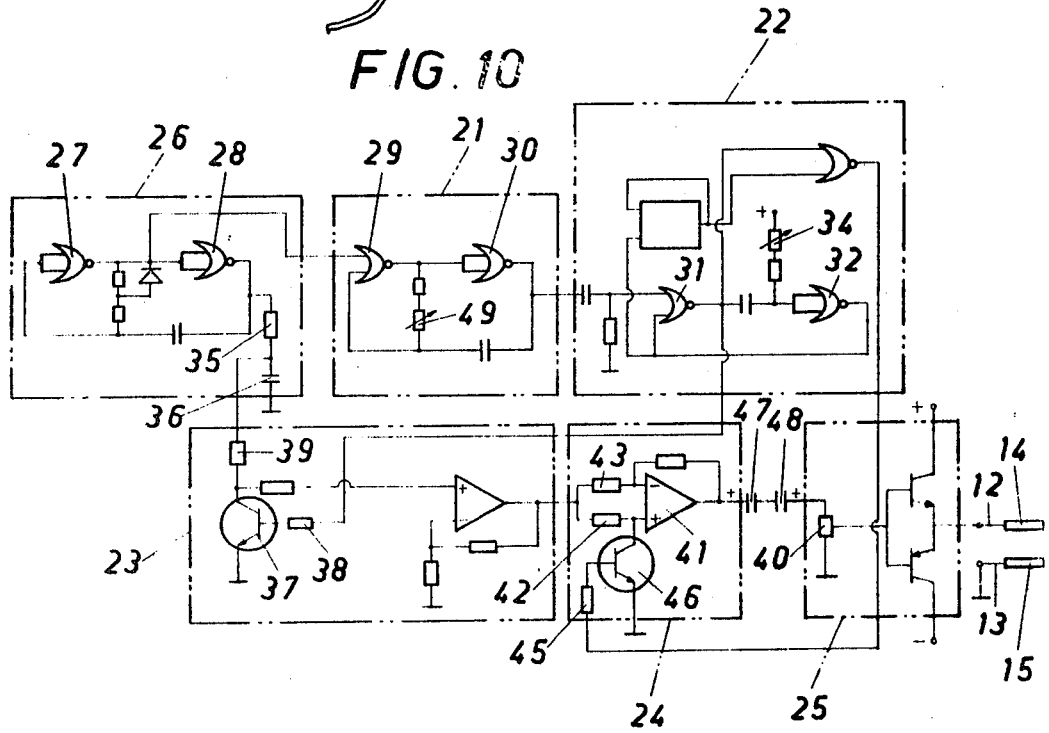
FIG. 10 shows an example of a circuit for use with the pulse generator.

The function of the pulse generator will now be described with reference to the block diagram according to FIG. 9, in which the circuit according to FIG. 10 has been divided into blocks numbered from 21 to 26.

The pulse generator according to FIG. 9 comprises a first block, an oscillator 21, delivering an electric signal in the form of a monophasic pulse train A, e.g. either positive or negative pulses, a second block, a pulse former 22, effecting the length of the pulses B, a third block, an envelope generator 23, which increases the amplitude of the pulses C gradually, a fourth block, a biphase generator 24, which converts the monophasic pulse form C to a biphasic pulse form D, a fifth block, a power amplifier 25, which amplifies the pulse train D delivering the amplified pulse train E, a sixth block, an interval generator 26 effecting the length of the pulse trains D and the break F between the pulse trains. Besides the above mentioned blocks 21–26 there are blocks for indicating the voltage of the current source and for reducing the supply voltage to certain components in the circuit with the intention of decreasing the power consumption.

Since a low energy consumption is essential at practical use of the stimulator and since it besides that has proved that a continuous electrical stimulation is not necessary for obtaining a maximum stimulating effect a block, an interval generator 26, has been provided, said interval generator 26 comprises two nor-gates 27 and 28, which continuously deliver a preferably square topped pulse train G with the frequency and pulse width adjusted so that the oscillator 21, which also comprises two nor-gates 29 and 30 and is controlled by the pulse train G, is activated (operates) only during e.g. 8–12 sec., after which a break of e.g. 15–20 sec. follows. This course is then continuously repeated as long as the pulse generator is switched on. The oscillator 21 generates an electric signal in the form of a pulse train A with square topped pulses and with a frequency, which by means of a potentiometer 49 can be varied preferably between 5–200 Hz and said pulse train A is delivered to the pulse former 22. The pulse former 22 comprises two nor-gates 31 and 32 and determines by means of a potentiometer 34 the length of the pulses B within the range 0,1–5 ms. The interval generator 26 delivers by means of the resistor 35 and the condenser 36 a second electric signal H with a saw tooth form intended to control the envelope generator 23, which comprises a transistor 37 and two resistors 38 and 39, in which the amplitude of the pulses in the pulse train B is gradually increased from a zero level until an optional maximum amplitude determined by a potentiometer 40 is reached. The stimulating amplitude is within the range 0–15V. It can e.g. be mentioned that for obtaining bladder relaxation a frequency of about 10 Hz and a pulse length of about 2 ms can be chosen and for obtaining urethra closure a frequency of about 50 Hz and a pulse length of about 1 ms can be appropriate. It must however be pointed out that these values are very individual and must be tested out for every patient. The optimum amplitude is more individually dependent than the frequency and the pulse length, the optimum amplitude is e.g. dependent on the age of the patient. The gradual amplitude increase of the stimulating signal D is essential for the practical use of the pulse generator, since the patient otherwise can feel the intermittently occuring stimulating signals D as unpleasant.

Practical tests have proved that electric signals comprising pulses with the same polarity, i.e. a monophasic pulse form, create a non-conductive layer at the positive electrode and thus it is important to deliver a biphasic signal to the electrodes. This is according to the invention achieved by a biphase generator 24 being arranged in connection with the envelope generator 23, so that every other incoming pulse is given a positive and every other a negative amplitude and said biphase generator 24 comprises an operation amplifier 41, four resistors 42, 43, 44 and 45 and a transistor 46. The pulse train D obtained is then amplified in the power amplifier 25, in which the degree of amplification can be adjusted by means of the potentiometer 40, and is delivered to the electrodes 14 and 15 by at least two wires 12 and 13 resp. In order to prevent tissue damages e.g. when a battery becomes out of function condensers 47 and 48 are arranged between the biphase generator 24 and the power amplifier 25.

As is previously mentioned the pulse generator also comprises a block (not shown) for controlling and indicating the voltage of the batteries, so that the patient becomes aware of when it is time to change batteries owing to that the capacity has decreased very much. An illuminating diode is lightened during about 2 sec. every time the patient switches the apparatus on, if the voltage of the positive battery is above e.g. 7,5V. The illuminating diode is then darkened automatically. If the illuminating diode would not be lightened it is time for a change of batteries.

The invention is of course not limited to the above described examples but can be varied within the scope of the claims. It is e.g. possible to combine features of the different embodiments. The examples have been described with reference to urinary incontinence, but the same advantages are achieved for faecal incontinence.

What I claim is:

1. An electical stimulator comprising an obturator intended to be worn within the vagina or anus, said obturator being provided with electrodes energized by a pulse generator and thereby controlling the urethral-, the bladder and/or the rectal function, and said obturator being made of a flexible material, which is expandable and thus provides a safe fixation of the obturator within the body, wherein the obturator is provided with a substantially plane or somewhat curved end gable at its inner end as seen from its position of use, the electrodes being arranged in two groups arranged at a certain distance from each other, each group being electrically connected to the pulse generator and comprising a number of electrode plates connected in parallel and arranged in substantially the same plane, the electrode plates of both grops being directed towards the same direction and the electrode plates of each group extending over only a part of the circumference of the obturator for achieving a directional stimulating effect.

2. An electrical stimulator as claimed in claim 1, wherein the electrode plates of each group are arranged at substantially the same distance from said end gable of the obturator.

3. An electrical stimulator as claimed in claim 1, wherein said plane makes an angle of 45°–90° with the longitudinal axis of the obturator.

4. An electrical stimulator as claimed in claim 1, wherein the electrode plates of each group extends over a part of the circumference of the obturator corresponding to a sector, the limiting radii of which make an angle of about 80°–240° with each other.

5. An electrical stimulator as claimed in claim 1, wherein the obturator has a thicker wall thickness on the side provided with the electrodes.

6. An electrical stimulator as claimed in claim 1, wherein the obturator on the side not provided with the electrodes is provided with one or more bulges, which preferably are integral with the obturator.

7. An electrical stimulator as claimed in claim 1, wherein the obturator at its part below the electrodes has a thinner wall thickness than the upper part provided with the electrodes.

8. An electrical stimulator as claimed in claim 1, wherein the electrodes in each group are arranged in double or multiple rows.

9. An electrical stimulator as claimed in claim 1, wherein the pulse generator provides an intermittent stimulation.

10. An electrical stimulator as claimed in claim 1, wherein the pulse generator comprises a first circuit block, an envelope generator, generating a pulse train with a gradually increasing amplitude up to an optional maximum amplitude, a second block, a biphase generator, generating a biphasic pulse train with every other pulse negative and every other pulse positive, and a third block, an interval generator, controlling the length of the pulse trains and the break between the appearances of the pulse trains.

11. An electrical stimulator as claimed in claim 10, wherein the envelope generator receives two electric signals, one of which consisting of pulses with a saw tooth form and the other of square topped pulses, said signals being converted by the envelope generator delivering an outgoing signal in the form of a pulse train with a gradually increasing amplitude up to the adjusted maximum amplitude during every unit of stimulation pulses.

12. An electrical stimulator as claimed in claim 10, wherein said envelope generator comprises a first input, which by a first resistor is connected to the collector of a transistor, and a second input, which by a second resistor is connected to the base of said transistor, and an outgoing signal is obtained and is delivered by means of a third resistor connected to the collector of said transistor.

13. An electrical stimulator as claimed in claim 10, wherein said biphase generator receives two electric monophasic signals substantially square topped, said signals being converted in the biphase generator and thus providing a biphasic outgoing signal.

14. An electrical stimulator as claimed in claim 13, wherein the biphase generator comprises a first input connected to a first and a second resistor, which are connected to the positive and negative input-resp, of an operation amplifier, and a second input, which by a third resistor is connected to the base of a transistor, the collector of which is connected to the positive input of said operation amplifier, and a fourth resistor is connected between the negative input and output of the operation amplifier, said fourth resistor determines the degree of amplification in the circuit.

15. An electrical stimulator as claimed in claim 10, wherein the generated pulse frequency is within the range 5-200 Hz.

16. An electrical stimulator as claimed in claim 15, wherein the length of the generated pulses is within the range 0,1-5 ms.

17. An electrical stimulator as claimed in claim 10, wherein the length of the pulse trains is about half the time of the breaks between the appearances of the pulse trains.

* * * * *